United States Patent [19]
Feingold

[11] Patent Number: 5,913,898
[45] Date of Patent: Jun. 22, 1999

[54] INTRAOCULAR CONTACT LENS AND METHOD OF IMPLANTATION

[75] Inventor: Vladimir Feingold, Laguna Niguel, Calif.

[73] Assignee: Staar Surgical Company, Inc., Monrovia, Calif.

[21] Appl. No.: 08/755,886

[22] Filed: Dec. 2, 1996

Related U.S. Application Data

[63] Continuation of application No. 08/318,991, Oct. 6, 1994, abandoned.

[51] Int. Cl.⁶ ........................................................ A61F 2/16
[52] U.S. Cl. ................................................................ 623/6
[58] Field of Search ............................................. 623/5, 6

[56] References Cited

U.S. PATENT DOCUMENTS

| | | | |
|---|---|---|---|
| 4,192,022 | 3/1980 | LaHaye | 623/6 |
| 4,449,257 | 5/1984 | Koeniger | 623/6 |
| 4,585,456 | 4/1986 | Blackmore | 623/6 |
| 4,673,406 | 6/1987 | Schlegel | 623/6 |
| 4,769,035 | 9/1988 | Kelman | 623/6 |
| 4,795,462 | 1/1989 | Grendahl | 623/5 X |
| 4,816,032 | 3/1989 | Hetland | 623/6 |
| 4,932,970 | 6/1990 | Portney | 623/6 |
| 4,994,080 | 2/1991 | Shepard | 623/6 X |
| 5,092,880 | 3/1992 | Ohmi | 623/6 |
| 5,104,590 | 4/1992 | Blake | 623/6 X |
| 5,133,747 | 7/1992 | Feaster | 623/6 |
| 5,147,393 | 9/1992 | Van Noy et al. | 623/6 |
| 5,152,787 | 10/1992 | Hamblen | 623/6 |
| 5,192,318 | 3/1993 | Schneider et al. | 623/6 |
| 5,258,025 | 11/1993 | Fedorov et al. | 623/6 |
| 5,344,648 | 9/1994 | Schneider et al. | 623/6 |
| 5,480,428 | 1/1996 | Fedorov et al. | 623/6 |

FOREIGN PATENT DOCUMENTS

| | | | |
|---|---|---|---|
| 477109 | 3/1992 | European Pat. Off. | 623/6 |
| 2666735 | 3/1992 | France | 623/6 |
| 1034325 | 7/1958 | Germany | 623/6 |
| 9220302 | 11/1992 | WIPO | 623/6 |

OTHER PUBLICATIONS

Kendall, Claud, "Ultrafocal Bifocal Contact Lens" Jan. 1976, pp. 31–35.

*Primary Examiner*—David H. Willse
*Attorney, Agent, or Firm*—Klima & Pezzlo, P.C.

[57] ABSTRACT

An intraocular contact lens for implantation into the eye. The intraocular contact lens is provided with a transition between a lens portion and lens body portion to minimize edge formation that could potentially damage or wear the back of the iris. Further, the intraocular contact lens can have a variety of features including a groove on the anterior surface for enhancing lubrication between the intraocular contact lens and the back of the iris, an air passageway for equalizing the pressure between the anterior surface and posterior surface, and one or more indents for manipulating the intraocular contact lens under the eye during the implantation operation while preventing contact of the natural lens with the tip of the manipulating instrument.

25 Claims, 13 Drawing Sheets

| IC2020 (POSITIVE) ||||
|---|---|---|---|
| DIOPTER NOMINAL | Tc ± 0.05 | Do ± 0.1 | Rfr NOMINAL |
| 3.0 | 0.18 | 4.50 | 7.91 |
| 3.5 | 0.20 | 4.50 | 7.65 |
| 4.0 | 0.22 | 4.50 | 7.40 |
| 4.5 | 0.23 | 4.50 | 7.16 |
| 5.0 | 0.24 | 4.50 | 6.95 |
| 5.5 | 0.25 | 4.50 | 6.74 |
| 6.0 | 0.27 | 4.50 | 6.55 |
| 6.5 | 0.28 | 4.50 | 6.36 |
| 7.0 | 0.29 | 4.50 | 6.19 |
| 7.5 | 0.30 | 4.50 | 6.02 |
| 8.0 | 0.32 | 4.50 | 5.87 |
| 8.5 | 0.33 | 4.50 | 5.72 |
| 9.0 | 0.34 | 4.50 | 5.58 |
| 9.5 | 0.35 | 4.50 | 5.45 |
| 10.0 | 0.36 | 4.50 | 5.32 |
| 10.5 | 0.38 | 4.50 | 5.20 |
| 11.0 | 0.39 | 4.50 | 5.08 |
| 11.5 | 0.40 | 4.50 | 4.97 |
| 12.0 | 0.40 | 4.37 | 4.86 |
| 12.5 | 0.40 | 4.29 | 4.76 |
| 13.0 | 0.40 | 4.20 | 4.66 |
| 13.5 | 0.40 | 4.13 | 4.57 |
| 14.0 | 0.40 | 4.05 | 4.48 |
| 14.5 | 0.40 | 4.00 | 4.39 |
| 15.0 | 0.45 | 4.00 | 4.31 |
| 15.5 | 0.45 | 4.00 | 4.23 |
| 16.0 | 0.45 | 4.00 | 4.15 |
| 16.5 | 0.45 | 4.00 | 4.08 |
| 17.0 | 0.45 | 3.96 | 4.01 |

| IC2020 (NEGATIVE) | | | | | | |
|---|---|---|---|---|---|---|
| DIOPTER NOMINAL | Tc±0.05 | Tm±0.05 | Do±0.1 | Rfr | Rfr2 | Ro |
| | | | | NOMINAL | | |
| −3.0 | 0.21 | 0.30 | 5.0 | 13.64 | 8.93 | 10.00 |
| −3.5 | 0.20 | 0.30 | 5.0 | 14.51 | 8.93 | 10.00 |
| −4.0 | 0.19 | 0.30 | 5.0 | 15.50 | 8.93 | 10.00 |
| −4.5 | 0.17 | 0.30 | 5.0 | 16.64 | 8.93 | 10.00 |
| −5.0 | 0.16 | 0.30 | 5.0 | 17.96 | 8.93 | 10.00 |
| −5.5 | 0.14 | 0.30 | 5.0 | 19.51 | 8.93 | 10.00 |
| −6.0 | 0.13 | 0.30 | 5.0 | 21.34 | 8.93 | 10.00 |
| −6.5 | 0.12 | 0.30 | 5.0 | 23.56 | 8.93 | 10.00 |
| −7.0 | 0.10 | 0.30 | 5.0 | 26.30 | 8.93 | 10.00 |
| −7.5 | 0.09 | 0.30 | 5.0 | 29.76 | 8.93 | 10.00 |
| −8.0 | 0.07 | 0.30 | 5.0 | 34.26 | 8.93 | 10.00 |
| −8.5 | 0.06 | 0.30 | 5.0 | 40.38 | 8.93 | 10.00 |
| −9.0 | 0.12 | 0.35 | 4.8 | 49.18 | 8.76 | 10.00 |
| −9.5 | 0.10 | 0.35 | 4.8 | 62.83 | 8.76 | 10.00 |
| −10.0 | 0.09 | 0.35 | 4.8 | 86.99 | 8.76 | 10.00 |
| −10.5 | 0.08 | 0.35 | 4.8 | 141.34 | 8.76 | 10.00 |
| −11.0 | 0.07 | 0.35 | 4.8 | 376.86 | 8.76 | 10.00 |
| −11.5 | 0.09 | 0.35 | 4.5 | 100000 | 8.78 | 9.83 |
| −12.0 | 0.08 | 0.35 | 4.5 | 100000 | 8.78 | 9.42 |
| −12.5 | 0.07 | 0.35 | 4.5 | 100000 | 8.78 | 9.04 |
| −13.0 | 0.10 | 0.40 | 4.5 | 100000 | 8.61 | 8.69 |
| −13.5 | 0.09 | 0.40 | 4.5 | 100000 | 8.61 | 8.37 |
| −14.0 | 0.08 | 0.40 | 4.5 | 100000 | 8.61 | 8.07 |
| −14.5 | 0.07 | 0.40 | 4.5 | 100000 | 8.61 | 7.79 |
| −15.0 | 0.11 | 0.45 | 4.5 | 100000 | 8.46 | 7.53 |
| −15.5 | 0.09 | 0.45 | 4.5 | 100000 | 8.46 | 7.29 |
| −16.0 | 0.08 | 0.45 | 4.5 | 100000 | 8.46 | 7.06 |
| −16.5 | 0.07 | 0.45 | 4.5 | 100000 | 8.46 | 6.85 |
| −17.0 | 0.06 | 0.45 | 4.5 | 100000 | 8.46 | 6.65 |

|  |  |  |  |
|---|---|---|---|
|  |  | Example − (100ph2, − 10 Diopter) | |
|  |  |  |  |
|  |  | R1[mm] | 100000.00 |
|  |  | R2[mm] | 11.96 |
|  |  | R3[mm] | 13.60 |
|  |  | R4[mm] | 15.75 |
|  |  | R5[mm] | 18.70 |
|  |  | R6[mm] | 10.00 |
|  |  | R7[mm] | 8.96 |

INTRAOCULAR CONTACT LENS AND METHOD OF IMPLANTATION

This application is a Continuation of application Ser. No. 08/318,991, filed on Oct. 6, 1994, now abandoned.

FIELD OF THE INVENTION

This invention relates to intraocular contact lens and methods of implanting intraocular contact lens in the eye. Specifically this invention relates to contact lens for surgical implantation in the human eye, and to methods of implanting an intraocular contact lens in the human eye.

BACKGROUND OF THE INVENTION

Traditionally, contact lens were developed and marketed for use on the exterior surface of the eye. The contact lens were initially all made from glass material, however, glass has been substantially replaced with synthetic plastic materials, particularly materials that minimize any reaction by the eye.

Figure 27:
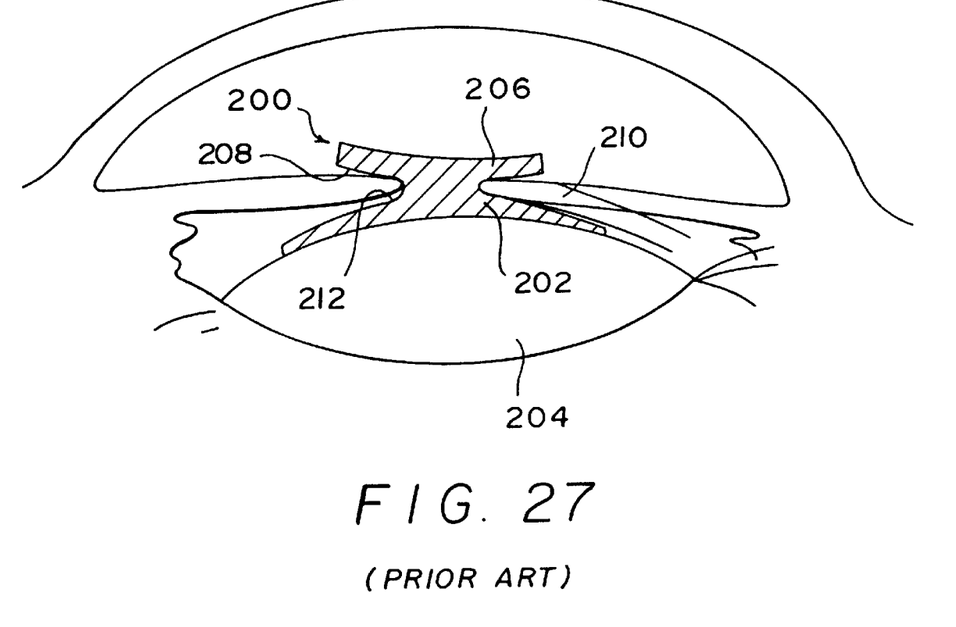
FIG. 27 is a cross-sectional view of the eye with a prior art intraocular contact lens implanted therein.

In 1989, the Russians disclosed a silicone intraocular contact lens. FIG. 27 shows an eye fitted with the Russian intraocular contact lens revealing its method of attachment in the eye. Specifically, the intraocular contact lens 200 includes a curved lens body 202 in contact with the natural crystalline eye lens 204. In the center of the curved lens body 202 extends a protrusion 206 defining an annular groove 208 with the curved lens body 202. The protrusion 206 is fitted through the iris 210 so that the inner circular edge 212 of the iris 210 is received within the annular groove 208.

Figure 28:
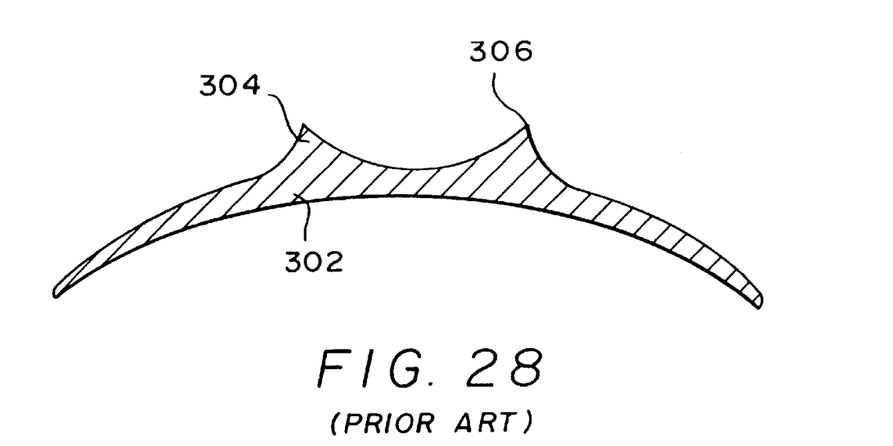
FIG. 28 is a cross-sectional view of another embodiment of a prior art intraocular contact lens.

In 1991, the Russians again disclosed a new silicone intraocular lens 300. FIG. 28 shows a transverse cross-sectional view of the intraocular lens having a curved body portion 302 with an annular protrusion 304. The annular protrusion 304 defines a substantially sharp circular edge 306. This particular lens has experienced some difficulties in use due to the substantially sharp circular edge 306 scraping against the inside surface of the iris repeatedly when the iris changes size causing pigment from the iris to be scraped from the iris.

SUMMARY OF THE INVENTION

An object of the present invention is to provide an improved intraocular contact lens.

Another object of the present invention is to provide an intraocular contact lens having an outer surface curvature that minimizes wear or damage to the back surface of the iris.

Another further object of the present invention is to provide an intraocular contact lens with a smooth transition between the lens body portion and lens portion on the outer surface of the intraocular contact lens.

An even further object of the present invention is to provide an intraocular contact lens having at least one circular groove, in particular a circular groove, in the outer surface thereof.

Another further object of the present invention is to provide an intraocular contact lens through hole or passage between the posterior and anterior surface of the intraocular contact lens in order to equalize the intraocular pressure.

An object of the present invention is to provide an improved method of implantation of an intraocular contact lens.

These and other objects of the present invention can be provided by various concepts that improve the configuration and arrangement over prior art intraocular contact lenses.

The intraocular contact lens according to the present invention is provided with an outer radius of curvature between the lens body portion and the lens portion that smoothly transitions therebetween. Specifically, there exists a transition in the outer radius of curvature of the lens between the lens body portion and the center lens portion. It is important that the transition in the radius of curvature between these two portions or zones is such that there is minimum edge formation so as to prevent damage or wear to the back of the iris. A transition can be made that has a gradient of radius of curvature within very small dimensions at the transition between the lens body portion and the center lens portion so that the transition is smooth. Such an arrangement works well within the eye and does not appear to damage or wear the back of the iris, and is a significant improvement over the prior art intraocular contact lenses derived from Russia that do cause damage and wear to the back of the iris.

Another concept according to the present invention is to provide at least one groove in the anterior surface of the intraocular contact lens. The groove can be a single groove or a pattern of grooves, and the groove(s) can be circular shaped, straight shaped, curve shaped, or combinations of shapes thereof. Further, the cross-sectional shape of the groove can be one-half circle, square, V-shaped or other suitable cross-sectional shape.

The groove is preferably in the arrangement of a circular groove located in the lens body portion and surrounding the lens body. This circular groove allows for good circulation of eye fluid that facilitates lubrication between the intraocular contact lens and the back of the iris. Other groove configurations can be utilized, however, the circular configuration appears to work very well.

A further concept according to the present invention is to provide a passageway in the intraocular contact lens between the posterior and anterior surface of the intraocular contact lens to equalize the intraocular pressure between the anterior surface and posterior surface of the intraocular contact lens allowing for an equalization of pressure between the anterior chamber and posterior chamber of the eye. The passageway can be provided in a variety of different forms including grooves in the anterior surface and posterior surface that connect together forming a continuous air passageway, a hole or other type of air passageway through the thickness dimension of the intraocular contact lens at one or more specific locations. For example, both the anterior surface and posterior surface of the intraocular contact lens can be provided each with a circular shaped groove and a single radial outwardly extending groove extending from the circular groove to the edge of the intraocular lens with both radial outwardly extending grooves meeting at the same peripheral position providing a continuous air passageway connecting the circular shaped grooves. In another embodiment, preferably one or more holes are provided near the perimeter of the intraocular contact lens. In a further embodiment, more preferably, a hole is provided in the center of the intraocular contact lens along the optical axis of the intraocular contact lens that provides the best location for equalization of intraocular pressure, and does not effect the optics of the intraocular contact lens.

An even further concept is to provide blind holes in the anterior surface of the intraocular contact lens to be used in the process of lens insertion and positioning the intraocular contact lens under the iris without touching the natural lens.

The method of implanting an intraocular contact lens according to the present invention includes placing the intraocular lens in the posterior chamber of the eye between the natural human crystalline lens and the iris. Further, an important procedure in the implantation method includes providing one or more through holes in the iris to place the anterior chamber and posterior chamber in fluid communication to allow equalization of pressure therebetween. This prevents the intraocular contact lens being sucked into tight contact with the back of the iris potentially causing significant damage and wear to the back of the iris. This affect is due to a differential pressure between the posterior and anterior chambers. Thus, the one or more through holes alleviates the situation.

DETAILED DESCRIPTION OF PREFERRED EMBODIMENTS

Figure 1:
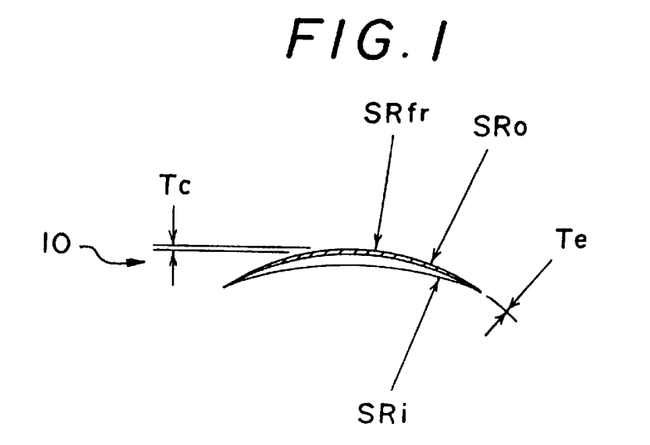
FIG. 1 is a cross-sectional view of a positive intraocular contact lens according to the present invention, as indicated in FIG. 3.
Figures 2, 3:
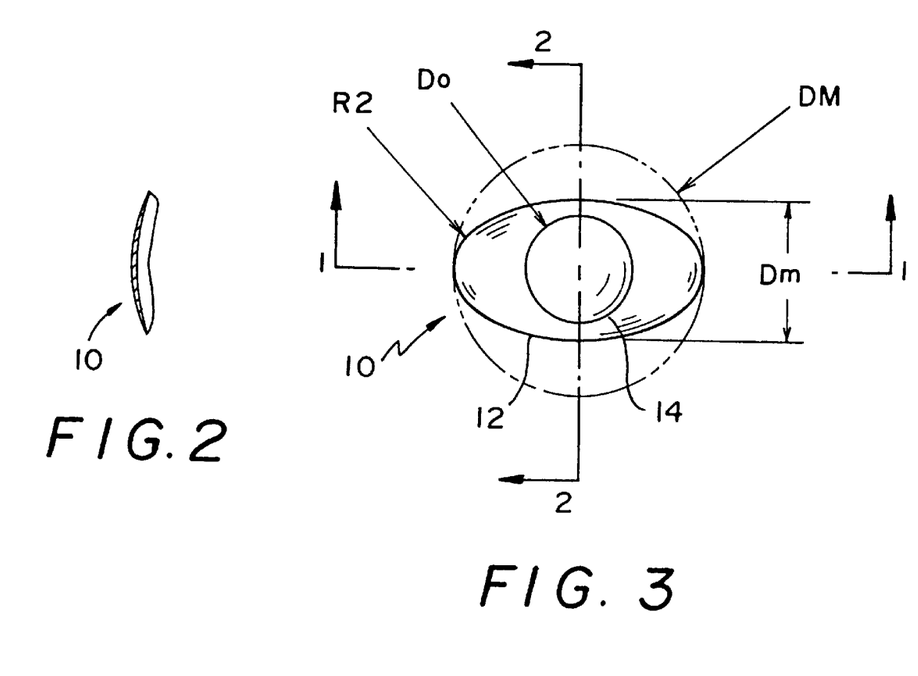
FIG. 2 is a cross-sectional view of the intraocular lens in FIG. 1, as indicated in FIG. 3.
FIG. 3 is a top planar view of the positive intraocular lens as shown in FIGS. 1 and 2.

An embodiment of a positive intraocular contact lens according to the present invention as shown in FIGS. 1–3.

The intraocular contact lens 10 is defined by an oval-shaped lens body portion 12 defined by major axis diameter DM and minor axis diameter Dm, and radius R2, and a circular shaped lens portion 14 having a diameter Do.

The lens portion 14 has a thickness Tc and the lens body portion 12 has an edge thickness Te, as shown in FIG. 1. Further, the lens portion 14 has a curvature SRfr, and the lens body portion 12 has an outer curvature SRo and an inner curvature Sri.

Figure 4:
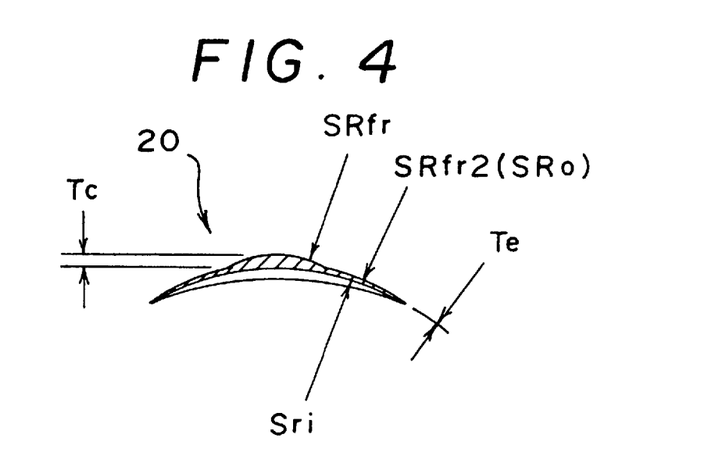
FIG. 4 is a cross-sectional view of another embodiment of a positive intraocular contact lens according to the present invention, as indicated in FIG. 6.
Figures 5, 6:
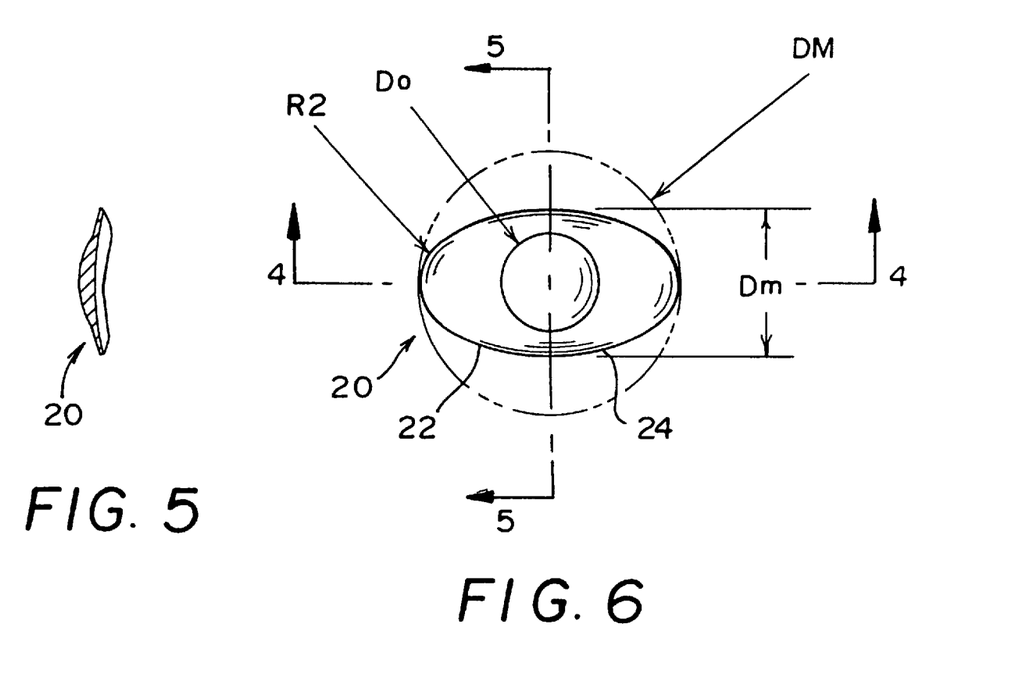
FIG. 5 is a cross-sectional view of the positive intraocular contact lens shown in FIG. 4, as indicated in FIG. 6.
FIG. 6 is a top planar view of the positive intraocular contact lens as shown in FIGS. 5 and 6.

Another embodiment of a positive intraocular contact lens according to the present invention is shown in FIGS. 4–6.

The intraocular contact lens 20 is defined by an oval-shaped lens body portion 22 defined by major axis diameter DM and minor axis diameter Dm, and a radius R2, and a circular shaped lens portion 24 having a diameter Do.

The lens portion 24 has a thickness Tc and the lens body portion 22 has an edge thickness Te, as shown in FIG. 4. Further, the lens portion 24 has a curvature SRfr and the lens body portion 22 has an outer curvature SRfr2 (SRo) and an inner curvature Sri.

Figure 7:
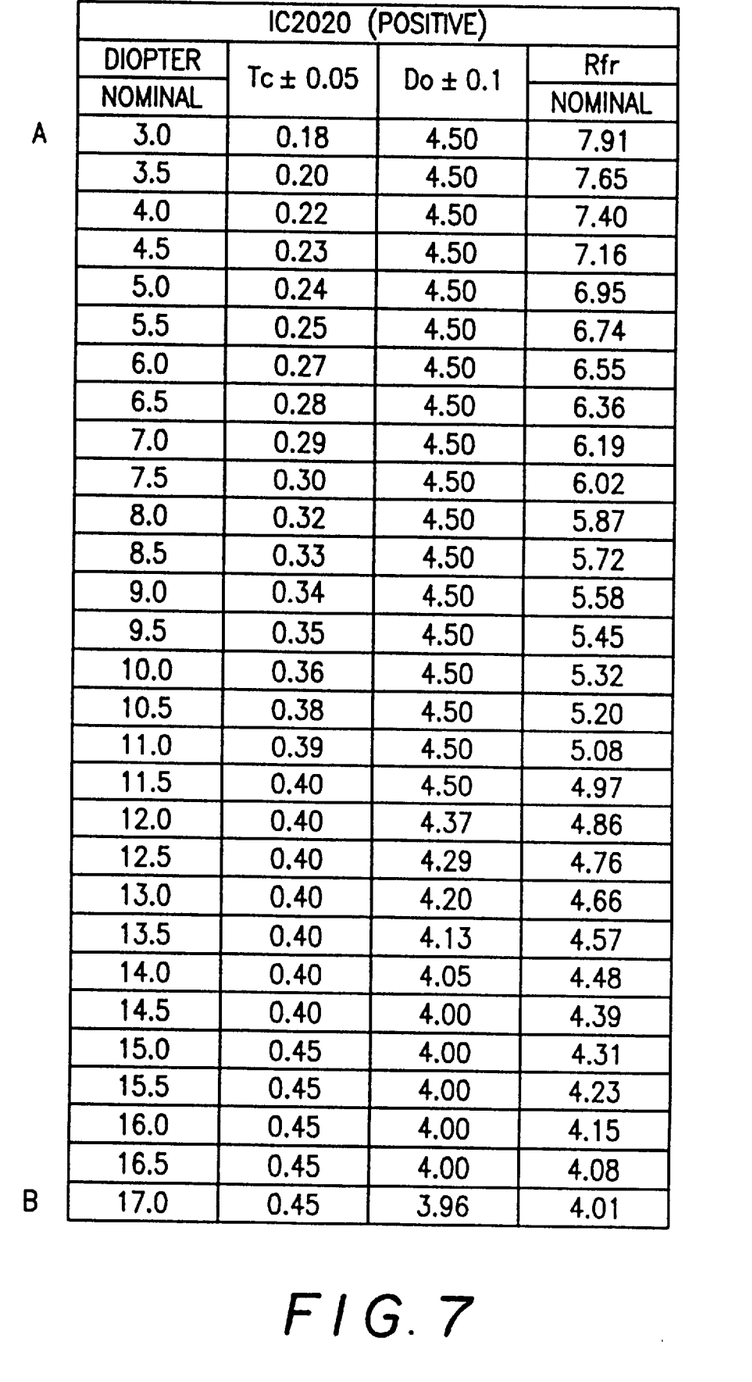
FIG. 7 is a table of examples of positive intraocular contact lenses directed to the two embodiments shown in FIGS. 1–6.

Specific examples of the positive intraocular contact lens are given in the table in FIG. 7. In these examples, T=0.05±0.02 mm, Sro=9.4±0.1, Sri=9.8, DM=10.5±0.1 mm, Dm=6±0.3 mm and R2±0.1.

Figure 8:
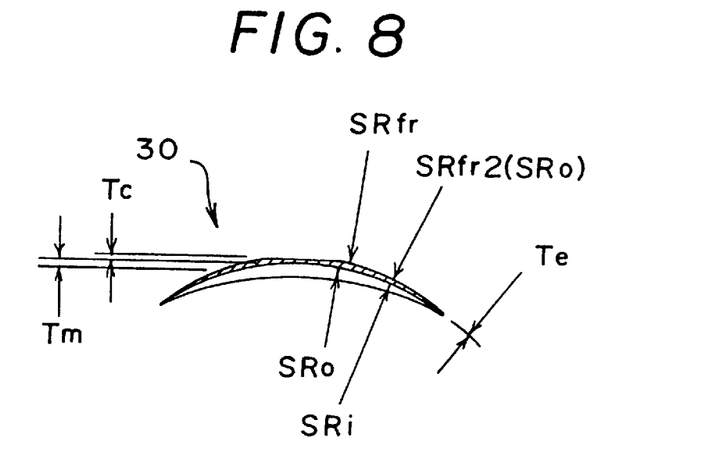
FIG. 8 is a cross-sectional view of a negative intraocular contact lens according to the present invention, as indicated in FIG. 10.
Figure 9:
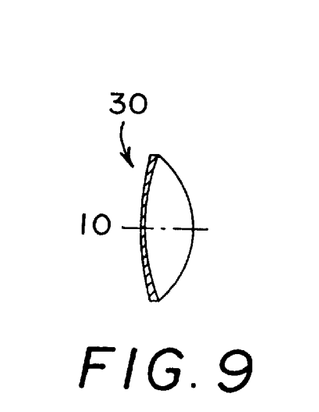
FIG. 9 is a cross-sectional view of the negative intraocular contact lens shown in FIG. 8, as indicated in FIG. 10.
Figure 10:
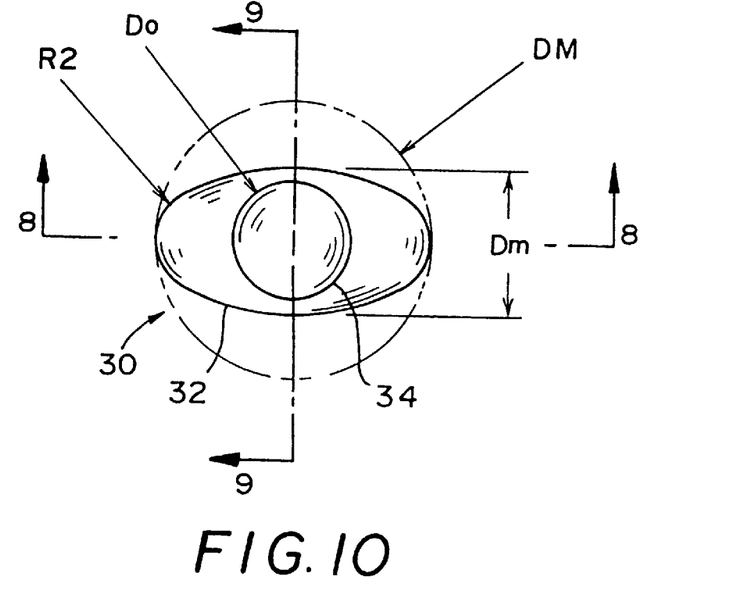
FIG. 10 is a top planar view of the negative intraocular contact lens shown in FIGS. 8 and 9.

An embodiment of a negative intraocular contact lens according to the present invention as shown in FIGS. 8–10.

The intraocular contact lens 30 is defined by an oval-shaped lens body portion 32 defined by major axis diameter DM and minor axis diameter Dm, and having a radius R2, and a circular shaped lens portion 34 having a diameter Do.

The lens portion 34 has a thickness Tc and the lens body portion 32 has an edge thickness Te, as shown in FIG. 8. Further, the lens portion 34 has a curvature SRfr and the lens body portion 32 has an outer curvature SRo and an inner curvature Sri.

Figure 11:
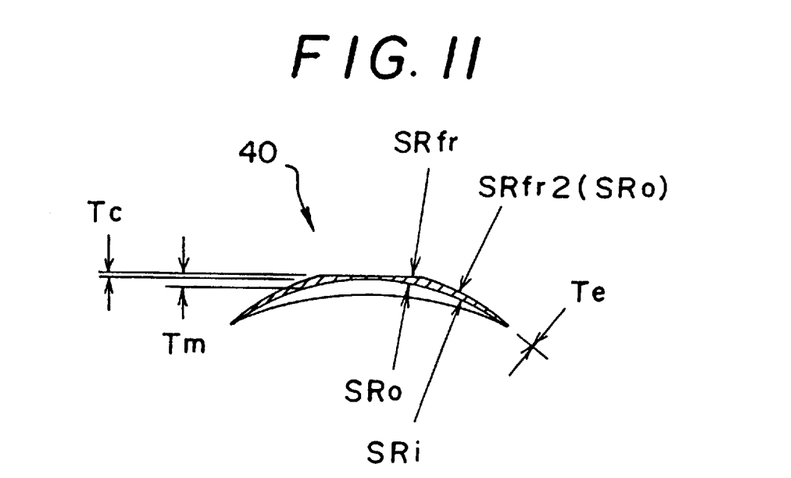
FIG. 11 is another embodiment of a negative intraocular contact lens according to the present invention, as indicated in FIG. 12.
Figures 12, 13:
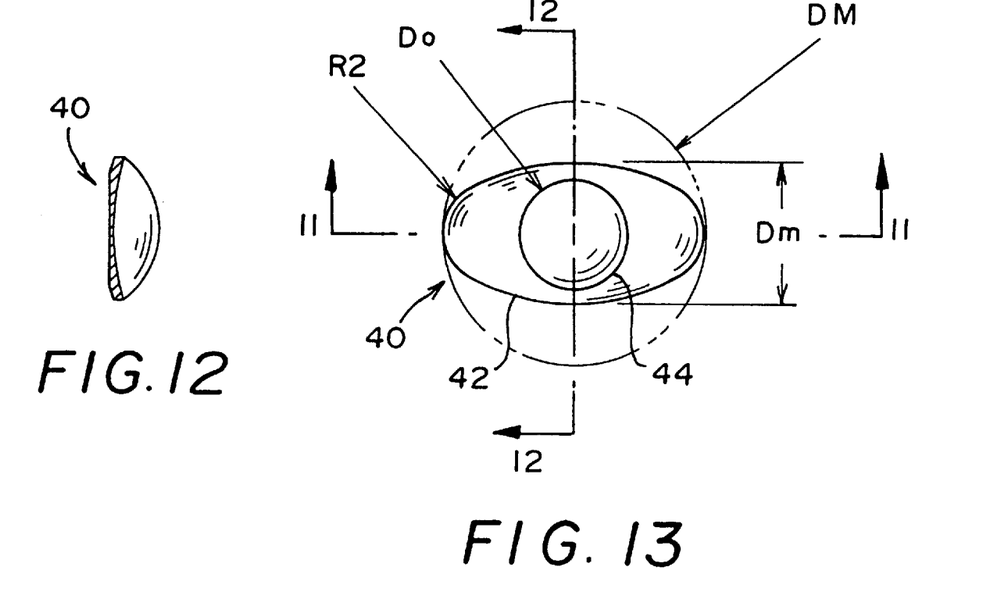
FIG. 12 is a cross-sectional view of the intraocular lens shown in FIG. 11, as indicated in FIG. 13.
FIG. 13 is a top planar view of the negative intraocular contact lens shown in FIGS. 11 and 12.

Another embodiment of a negative intraocular contact lens according to the present invention as shown in FIGS. 11–13.

The intraocular contact lens 40 is defined by an oval-shaped lens body portion 42 defined by major axis diameter DM and minor axis diameter Dm, and having a radius R2, and a circular shaped lens portion 44 having a diameter Do.

The lens portion 44 has a thickness Tc and the lens body portion 42 has an edge thickness Te, as shown in FIG. 11. Further, the lens portion 44 has a curvature SRfr and the lens body portion 42 has an outer curvature SRfr2 (SRo) and an inner curvature Sri.

Figure 14:
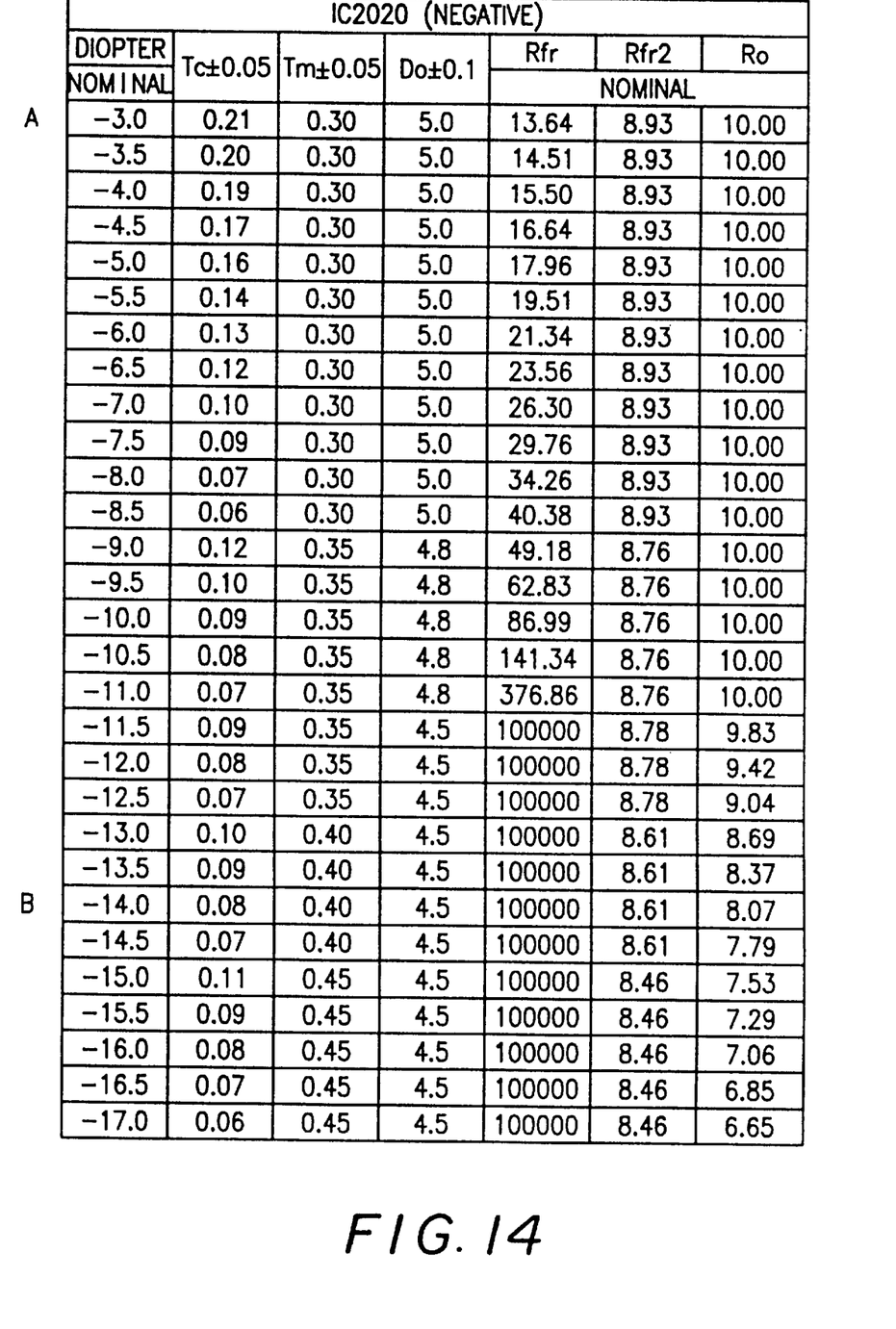
FIG. 14 is a table of examples of negative intraocular lenses directed to the two embodiments shown in FIG. 8–13.

Specific examples of the positive intraocular contact lens are given in the table in FIG. 14. In these examples, T=0.05±0.02 mm, Sro=9.4±0.1, Sri=9.8, DM=10.5±0.1 mm, Dm=6±0.3 mm and R2±0.1.

Figure 15:
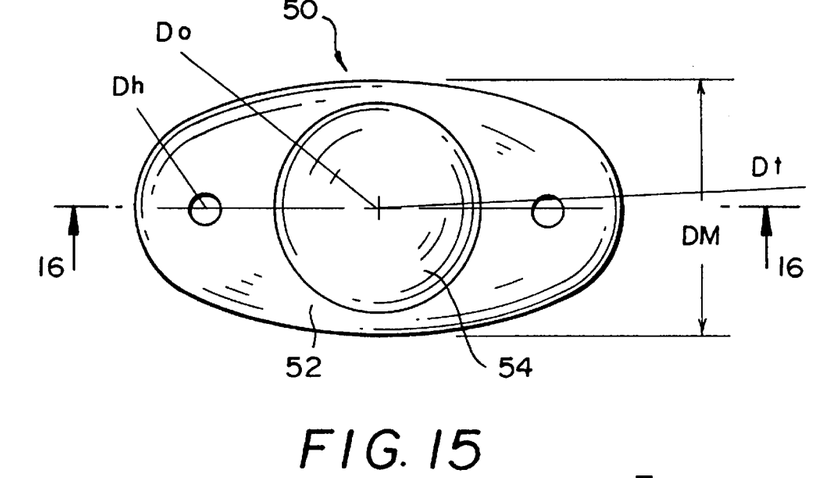
FIG. 15 is a top planar view of another embodiment of a positive intraocular contact lens according to the present invention.
Figure 16:
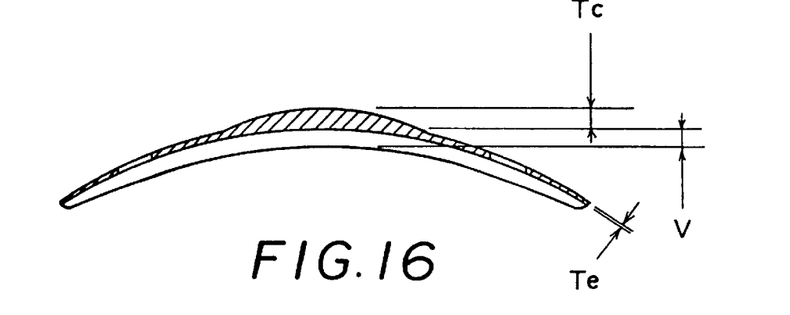
FIG. 16 is a cross-sectional view of the positive intraocular contact lens, as indicated FIG. 15.
Figure 17:
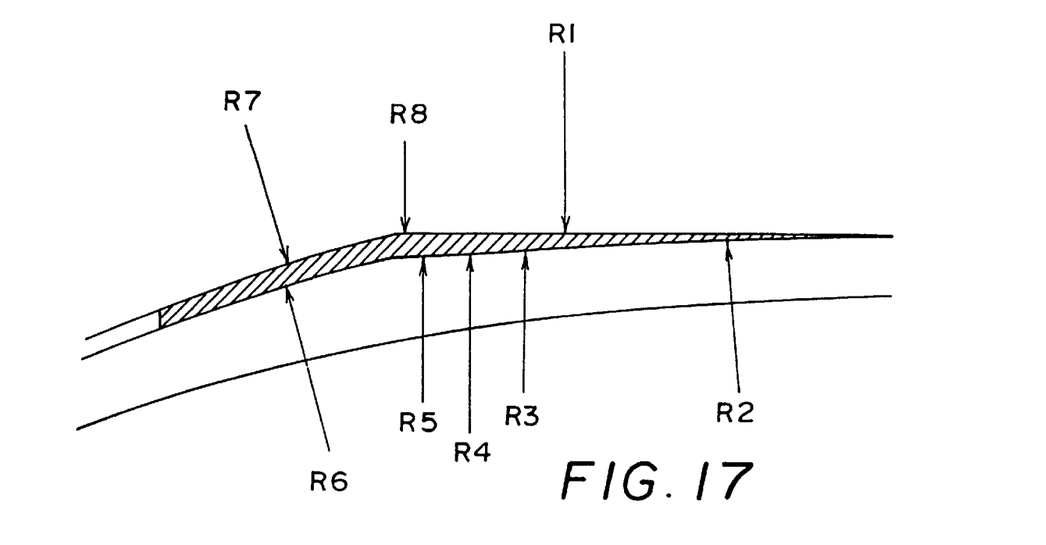
FIG. 17 is a partial detailed cross-sectional view of a portion of the positive intraocular lens shown in FIGS. 15 and 16, illustrating the detailed curvature thereof.

A further embodiment of a positive intraocular contact lens 50 is shown in FIGS. 15–17.

The intraocular contact lens 50 is defined by an oval-shaped lens body portion 52 defined by major axis diameter DM and minor axis diameter Dm, and radius R2, and a circular shaped lens portion 54 having a diameter Do. The lens portion 54 has a thickness Tc and the lens body portion 52 has an edge thickness Te, as shown in FIG. 16.

Figure 18:
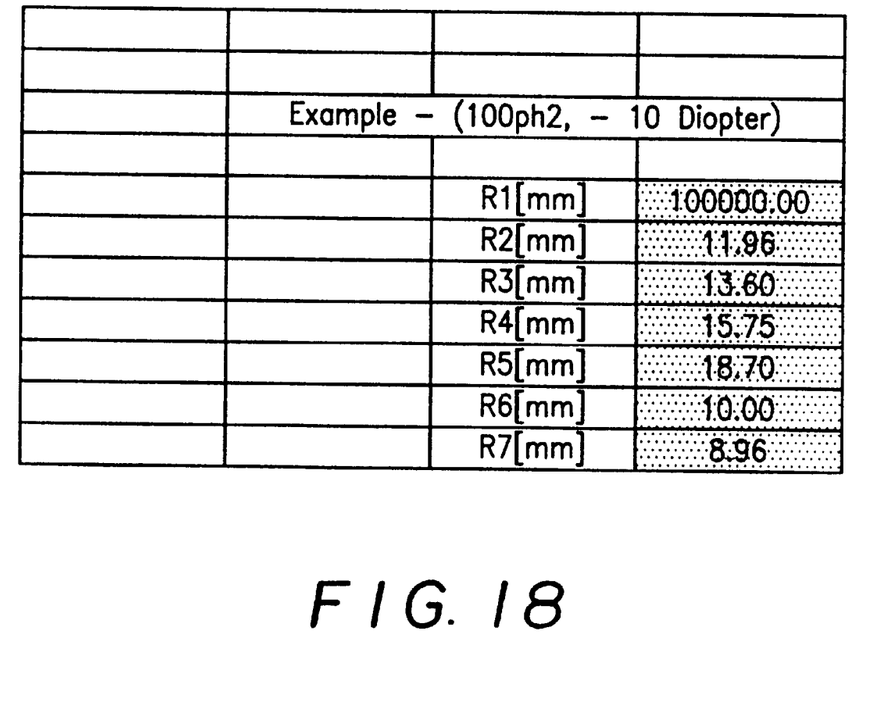
FIG. 18 is a table indicating the detailed curvature as an example of the embodiment of the positive intraocular lens shown in FIGS. 15–17.

The detail curvature of the intraocular contact lens is shown in FIG. 17. An example of this particular lens is given in the table in FIG. 18 with the designations R1–R8 corresponding to FIG. 17.

Figure 19:
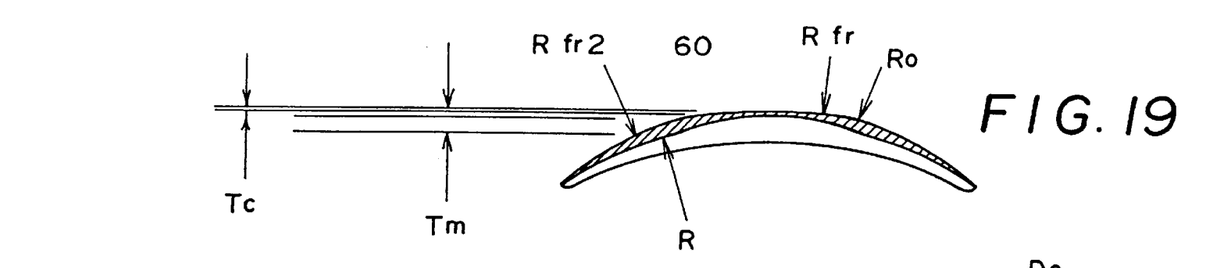
FIG. 19 is another embodiment of a negative intraocular contact lens according to the present invention.

A further embodiment of a negative intraocular contact lens 60 is shown in FIG. 19. The advantage of this embodiment is that a small gap exists between the intraocular contact lens center and the natural lens allowing for flow of body fluids, and to minimize friction which could potentially cause mechanical damage and cataracts in the eye.

Figure 20:
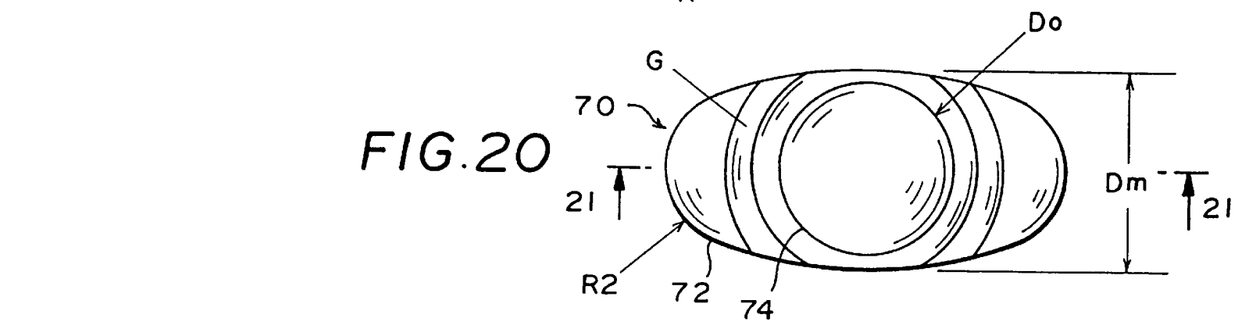
FIG. 20 is a top planar view of another negative intraocular contact lens according to the present invention with a circular groove in the lens body portion thereof.

An even further embodiment of a negative intraocular contact lens 70 is shown in FIG. 20.

Figure 21:
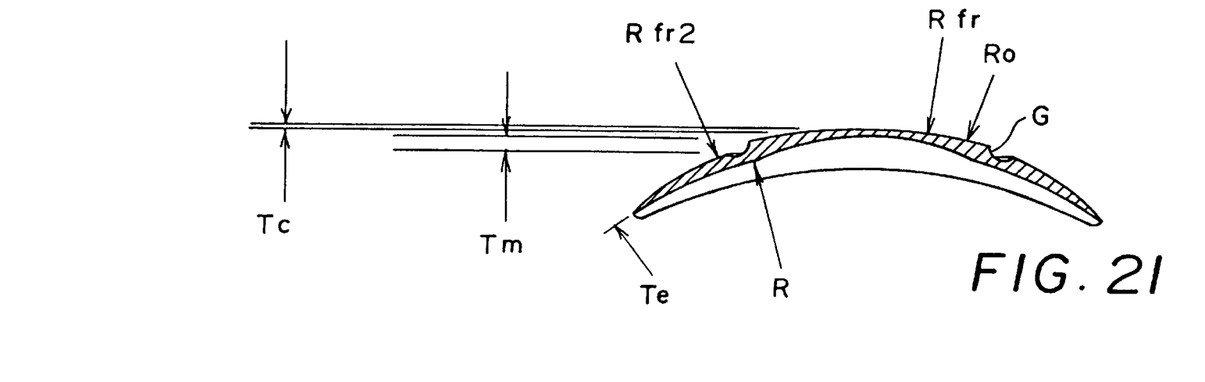
FIG. 21 is a cross-sectional view of the negative intraocular contact lens, as indicated in FIG. 20.

The intraocular contact lens 70 is defined by an oval-shaped lens body portion 72 defined by major axis diameter DM and minor axis diameter Dm, and a circular shaped lens portion 74 having a diameter Do. The lens portion 74 has a thickness Tc and the lens body portion 72 has an edge thickness Te, as shown in FIG. 21.

The important feature of this embodiment is the circular groove G provided in the lens body portion 72 surrounding the lens portion 74. The circular groove G allows for circulation of fluid inside the eye. Further, the groove G can be used for lens manipulation during surgery, and facilitates the equalization of intraocular pressure.

Figure 22:
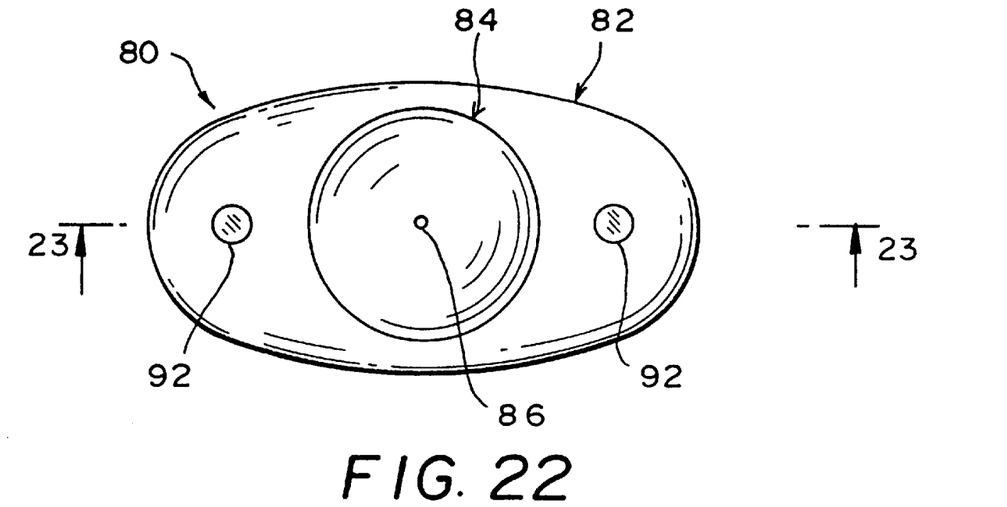
FIG. 22 is a top planar view of a preferred embodiment of an intraocular contact lens according to the present invention provided with a through hole in the optical center thereof.
Figure 23:
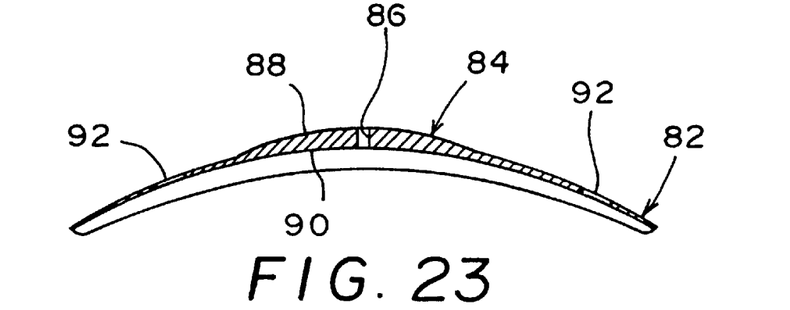
FIG. 23 is a cross-sectional view of the intraocular contact lens, as indicated in FIG. 20.

A preferred embodiment of an intraocular contact lens 80 having a lens body portion 82 and lens portion 84, as shown in FIGS. 22 and 23. In this embodiment, an air passageway 86 (e.g. hole) is provided in the center optical axis of the lens portion 84 for equalizing the pressure between the anterior surface 88 and posterior surface 90 of the intraocular contact lens 80. This air passageway 86 allows for equalization of pressure between the anterior chamber and posterior chamber of the eye. Otherwise, a significant suction or negative pressure can occur on the anterior surface of the intraocular contact lens sucking the back of the iris into contact therewith and causing damage or wear to the iris.

Figure 24:
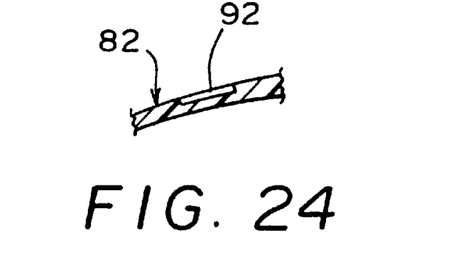
FIG. 24 is a cross-sectional view of intraocular contact lens according to the present invention.

The intraocular contact lens 80 is provided with a pair of indents 92, as shown in FIGS. 22 to 24, for allowing the intraocular contact lens 80 to be manipulated under the iris during the implantation operation. The indents 92 are significantly better than through holes for purposes of manipulation, since the bottoms of the indents prevent penetration of a manipulating tool through the lens and inadvertently into contact with the natural lens that would cause an immediate cataract of the natural lens.

Figure 25:
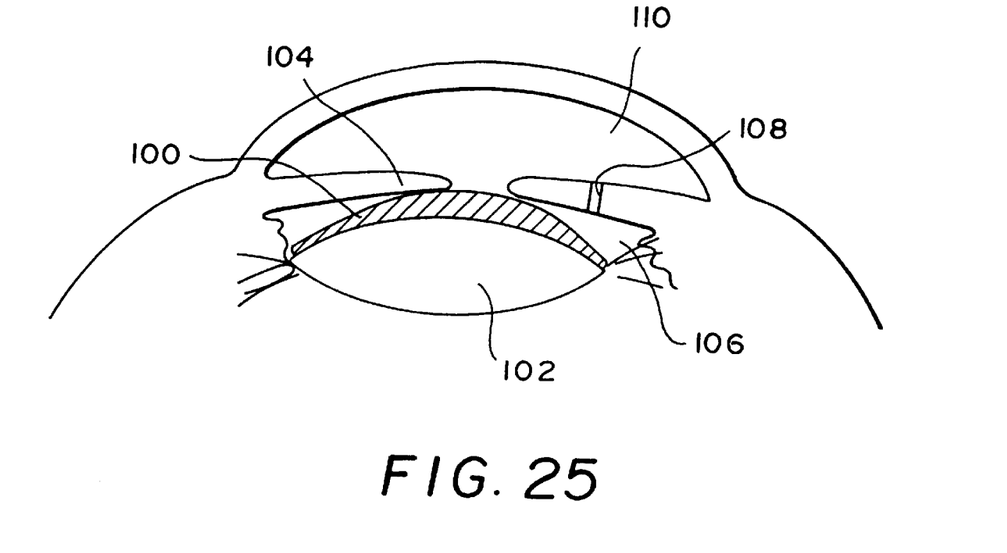
FIG. 25 is a top planar view of another embodiment of the intraocular contact lens according to the present invention with straight grooves.

Another embodiment of an intraocular contact lens according to the present invention is shown in FIG. 25, having a pair of straight grooves G'.

Figure 26:
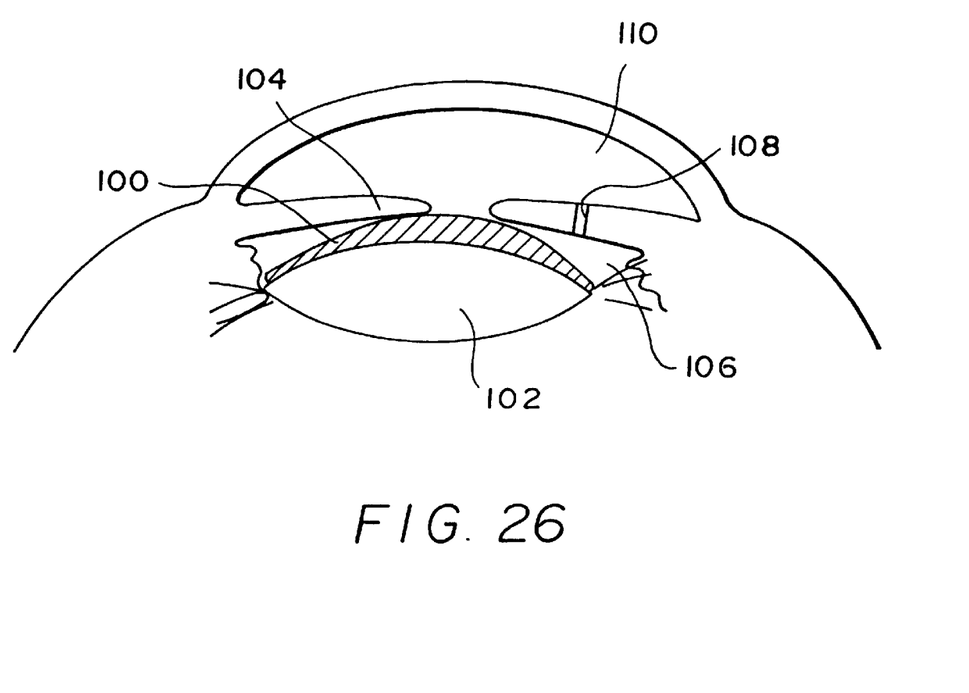
FIG. 26 is a cross-sectional view of the eye fitted with an intraocular contact lens according to the present invention with a through hole made in the iris.

FIG. 26 illustrates the manner in which an intraocular contact lens 100 according to the present invention is located in the eye.

The intraocular contact lens 100 is positioned over the natural crystalline lens 102 and underneath the iris 104. The intraocular contact lens 100 is located in the posterior chamber 106.

As an alternative or in addition to providing an air passageway in the intraocular contact lens between the anterior surface and posterior surface thereof, at least one through hole 108 can be provided in the iris 104 providing a conduit between the posterior chamber 106 and anterior chamber 110. The hole 108 allows for equalization of the pressure between the posterior chamber 106 and the anterior chamber 110 so that the iris 104 is not continuously sucked into contact with the intraocular contact lens potentially causing damage or wear to the back of iris 104.

I claim:

1. An intraocular contact lens for implantation into the eye, comprising:

a center lens portion having a first curvature;

a lens body portion extending from said center lens portion, said lens body portion having a second curvature different from said first curvature of said center lens portion;

a transition lens portion connecting said center lens portion to said lens body portion, said transition lens portion having predetermined dimensions and configured to provide a smooth transition of curvature from said center lens portion to said lens body portion such that there is minimum edge formation so as to prevent damage or wear to a back of an iris of an eye, wherein said center lens portion, transition lens portion, and said lens body portion define a continuous curved outer surface having a smooth curvature transition between an outer surface of said center lens portion and an outer surface of said lens body portion, and wherein the intraocular contact lens has a concave shaped surface to fit over an outer surface of a natural crystalline lens of the eye and at least one groove provided in an outer surface of the lens.

2. A lens according to claim 1, wherein said smooth curvature transition lens portion is defined by a gradient of varying outer surface curvature in a relatively small distance.

3. A lens according to claim 2, wherein a gradient of said smooth curvature transition between said center lens portion and said lens body portion is within the range of 2 to 6 diopter in power.

4. A lens according to claim 1, wherein said groove is a circular shaped groove.

5. A lens according to claim 4, wherein said circular groove is located in said outer surface of said lens body portion.

6. A lens according to claim 1, wherein said groove is a straight groove.

7. A lens according to claim 1, wherein said groove is a curved shaped groove.

8. A lens according to claim 1, including at least one passageway for equalizing the pressure between an anterior surface and posterior surface of the intraocular contact lens.

9. A lens according to claim 8, wherein said passageway is a hole through a thickness dimension of the intraocular contact lens.

10. A lens according to claim 9, wherein said hole is located in a center of said center lens portion.

11. A lens according to claim 9, wherein said hole is located in the center of an optical axis of the intraocular contact lens.

12. An intraocular contact lens for implantation into an eye, comprising:

a center lens portion;

a lens body portion surrounding said center lens portion; and at least one circular groove in an anterior surface of the lens to facilitate circulation of eye fluid wherein said groove has a half circle cross-sectional shape, wherein the intraocular contact lens has a concave shaped surface to fit over an outer surface of a natural crystalline lens of the eye, and wherein said center lens portion and said lens body portion define a continuous outer surface having a smooth transition between an outer surface of said center lens portion and an outer surface of said lens body portion.

13. A lens according to claim 12, wherein said circular groove is located in an anterior surface of said lens body portion.

14. A lens according to claim 12, including at least one passageway for equalizing the pressure between an anterior surface and posterior surface of the intraocular contact lens.

15. An intraocular contact lens for implantation into the eye, comprising:

a center lens portion having a first curvature;

a lens body portion extending from said center lens portion, said lens body portion having a second curvature different from said first curvature of said center lens portion;

a transition lens portion connecting said center lens portion to said lens body portion, said transition lens portion having predetermined dimensions and configured to provide a smooth transition of curvature from said center lens portion to said lens body portion such that there is minimum edge formation so as to prevent damage or wear to a back of an iris of an eye, wherein said center lens portion, transition lens portion, and said lens body portion define a continuous curved outer surface having a smooth curvature transition between an outer surface of said center lens portion and an outer surface of said lens body portion, and wherein the intraocular contact lens has a concave shaped surface to fit over an outer surface of a natural crystalline lens of the eye and at least one passageway for equalizing the pressure between an anterior surface and posterior surface of the intraocular contact lens.

16. A lens according to claim 15, wherein said smooth curvature transition lens portion is defined by a gradient of varying outer surface curvature in a relatively small distance.

17. A lens according to claim 16, wherein a gradient of said smooth curvature transition between said center lens portion and said lens body portion is within the range of 2 to 6 diopter in power.

18. A lens according to claim 15, including at least one groove provided in an outer surface of the lens.

19. A lens according to claim 18, wherein said groove is a circular shaped groove.

20. A lens according to claim 19, wherein said circular groove is located in said outer surface of said lens body portion.

21. A lens according to claim 18, wherein said groove is a straight groove.

22. A lens according to claim 18, wherein said groove is a curved shaped groove.

23. A lens according to claim 15, wherein said passageway is a hole through a thickness dimension of the intraocular contact lens.

24. A lens according to claim 23, wherein said hole is located in a center of said center lens portion.

25. A lens according to claim 23, wherein said hole is located in the center of an optical axis of the intraocular contact lens.

* * * * *